(12) United States Patent
Hafez (10) Patent No.: US 10,351,879 B2
(45) Date of Patent: Jul. 16, 2019

(54) METHOD AND SYSTEM FOR ELECTRO-ASSISTED HYDROGEN PRODUCTION FROM ORGANIC MATERIAL

(71) Applicant: GreenField Specialty Alcohols Inc., Toronto (CA)

(72) Inventor: Hisham Mohamed Hafez, London (CA)

(73) Assignee: GreenField Specialty Alcohols Inc., Toronto (CA)

( * ) Notice: Subject to any disclaimer, the term of this patent is extended or adjusted under 35 U.S.C. 154(b) by 168 days.

(21) Appl. No.: 15/219,881

(22) Filed: Jul. 26, 2016

(65) Prior Publication Data

US 2016/0333379 A1     Nov. 17, 2016

Related U.S. Application Data

(62) Division of application No. 13/768,449, filed on Feb. 15, 2013, now Pat. No. 9,458,474.

(Continued)

(51) Int. Cl.
    *C12P 3/00*     (2006.01)
    *C12M 1/26*     (2006.01)
    (Continued)

(52) U.S. Cl.
    CPC ............... *C12P 3/00* (2013.01); *C12M 21/04* (2013.01); *C12M 29/18* (2013.01); *C12M 33/22* (2013.01);
    (Continued)

(58) Field of Classification Search
CPC .. C05F 17/0235; C05F 17/02; C05F 17/0258; C05F 17/0205; C05F 17/027;
(Continued)

(56) References Cited

U.S. PATENT DOCUMENTS

| | | |
|---|---|---|
| 3,649,516 A | 3/1972 | Ernest, Jr. et al. |
| 4,491,522 A | 1/1985 | Ishida et al. |
| (Continued) | | |

FOREIGN PATENT DOCUMENTS

| | | |
|---|---|---|
| CA | 2751046 A1 | 8/2010 |
| CA | 2786751 A1 | 7/2011 |
| (Continued) | | |

OTHER PUBLICATIONS

Wang et al., "Integrated hydrogen production process from cellulose by combining dark fermentation, microbial fuel cells, and a microbial electrolysis cell", Bioresource Technology, Mar. 2011, vol. 102, pp. 4137-4143.

(Continued)

*Primary Examiner* — Michael L Hobbs
(74) *Attorney, Agent, or Firm* — Borden Ladner Gervals LLP (57) ABSTRACT

A method for producing hydrogen from organic material. Organic material and hydrogen-producing microorganisms are provided in a completely mixed bioreactor for breaking down the organic material into $H_2$, $CO_2$, fatty acids, and alcohols. $H_2$, $CO_2$, and a first liquid effluent are recovered from the completely mixed bioreactor. The first liquid effluent includes hydrogen-producing microorganisms, fatty acids, and alcohols. The first liquid effluent is provided into a gravity settler for separating the first liquid effluent into a concentrated biomass (including hydrogen-producing microorganisms) and a second liquid effluent (including at least a portion of the fatty acids and the alcohols). The concentrated biomass is provided into the completely mixed bioreactor. An input voltage is applied to at least one of the completely mixed bioreactor and the gravity settler for facilitating an electrohydrogenesis process therein.

15 Claims, 4 Drawing Sheets

Related U.S. Application Data (60) Provisional application No. 61/600,325, filed on Feb. 17, 2012.

(51) Int. Cl.

| | | |
|---|---|---|
| C12M 1/42 | (2006.01) | |
| C25B 1/02 | (2006.01) | |
| C12M 1/107 | (2006.01) | |
| C12M 1/00 | (2006.01) | |
| C25B 9/00 | (2006.01) | |
| C25B 1/00 | (2006.01) | |
| C25B 9/06 | (2006.01) | |

(52) U.S. Cl.
CPC ............... *C12M 35/02* (2013.01); *C25B 1/00* (2013.01); *C25B 1/02* (2013.01); *C25B 9/00* (2013.01); *C25B 9/06* (2013.01); *Y02E 50/343* (2013.01)

(58) Field of Classification Search
CPC .... C05F 17/0063; C12M 21/04; C12M 29/10; C12M 35/02; C12M 33/02; C25B 1/00; C25B 1/02; C25B 9/00; C25B 9/06; C25B 9/18; C12P 3/00; Y02E 50/343
See application file for complete search history.

(56) References Cited

U.S. PATENT DOCUMENTS

| | | | |
|---|---|---|---|
| 5,855,764 | A | 1/1999 | Greaney et al. |
| 7,439,047 | B2 | 10/2008 | Rozendal et al. |
| 2005/0194311 | A1 | 9/2005 | Rozich |
| 2008/0197074 | A1 | 8/2008 | Gallagher et al. |
| 2009/0317882 | A1* | 12/2009 | Cheng .............. C12M 21/04 435/167 |
| 2009/0325255 | A1* | 12/2009 | Chakravarti ........... C12M 21/04 435/168 |
| 2011/0011799 | A1 | 1/2011 | Rozendal et al. |
| 2011/0159559 | A1 | 6/2011 | Claassen et al. |
| 2011/0236946 | A1 | 9/2011 | MacLachlan et al. |

FOREIGN PATENT DOCUMENTS

| | | | |
|---|---|---|---|
| CN | 1856706 A | 11/2006 | |
| CN | 102300977 A | 12/2011 | |
| WO | 2005005981 A2 | 1/2005 | |
| WO | 2009034439 A2 | 3/2009 | |
| WO | 2010056460 A2 | 5/2010 | |
| WO | 2010085893 A1 | 8/2010 | |
| WO | WO-2010085893 A1 * | 8/2010 | ............ C12M 21/04 |

OTHER PUBLICATIONS

Written Opinion for Application No. PCT/CA2014/000600, dated Oct. 17, 2014, 8 pages.
Written Opinion for Application No. PCT/CA2014/051011, dated Jan. 16, 2015, 7 pages.
Wu et al., "HRT-dependent hydrogen production and bacterial community structure of mixed anaerobic microflora in suspended, granular and immobilized sludge systems using glucose as the carbon substrate", International Journal of Hydrogen Energy, Mar. 2008, vol. 33, pp. 1542-1549.
Zhang et al., "Biological hydrogen production by Clostridium acetobutylicum in an unsaturated flow reactor", Water Research, Feb. 2006, vol. 40, pp. 728-734.
Zhang et al. "Effect of hydraulic retention time on biohydrogen production and anaerobic microbial community", Process Biochemistry, vol. 41, issue 10, Oct. 2006, pp. 2118-2123
Zhang et al., "Rapid Formation of Hydrogen-Producing Granules in an Anaerobic Continuous Stirred Tank Reactor Induced by Acid Incubation", Biotechnology and Bioengineering, Apr. 15, 2007, 96, pp. 1040-1050.
Zhang et al., "The role of acid incubation in rapid immobilization of hydrogen-producing culture in anaerobic upflow column reactors", International Journal of Hydrogen Energy, Oct. 2008; 33, pp. 5151-5160.
Zverlov et al., "Bacterial acetone and butanol production by industrial fermentation in the Soviet Union: use of hydrolyzed agricultural waste for biorefinery", Appl Microbiol Biotechnol, May 10, 2006, 71, pp. 587-597.
Chinese Patent Application No. 201380019493.7, Office Action dated Oct. 26, 2016 with English summary.
Azbar et al., "State of the Art and Progress in Production of Biohydrogen", Bentham Science Publishers, Jun. 7, 2012, 262 pages.
Bankar et al., "Continuous two stage acetone-butanol-ethanol fermentation with integrated solvent removal using Clostridium acetobutylicum B 5313", Bioresource Technology, 2012, available online Dec. 8, 2011, vol. 106, pp. 110-116.
Chang et al., "Biohydrogen production with fixed-bed bioreactors", International Journal of Hydrogen Energy, vol. 27, Issues 11-12, Nov.-Dec. 2002, pp. 1167-1174.
Das et al., "Recent Developments in Biological Hydrogen Production Processes", Chemical Industry & Chemical Engineering Quarterly, accepted for publication Mar. 25, 2008, published 2008, vol. 14, No. 2, pp. 57-67.
Dayton et al., "Fuel Cell Integration—A Study of the Impacts of Gas Quality and Impurities", Chemistry of Bioengergy Systems Division of the National Bioenergy Centre, Milestone Completion Report, National Renewable Energy Laboratory, Jun. 2001, 28 pages.
El Naggar, "The Integrated Biohydrogen Reactor Clarifier System (IBRCS): Setup, Performance, and Application", Wastewater & Biosolids Treatment & Reuse: Bridging Modeling and Experimental Studies, Dr. Domenico Santoro, Trojan Technologies and Western University Eds, ECI Symposium Series, Jun. 8-14, 2014, retrieved from the Internet: http://dc.engconfintl.org/cgi/viewcontent.cgi?article= I 0 15&context=wbtr_i, pp. 1-28.
European Patent Application No. 13749197.3-1501 Supplementary Search Report dated Sep. 17, 2015.
Fang et al., "Effect of pH on hydrogen production from glucose by a mixed culture", Bioresource Technology, Mar. 2002, vol. 82, pp. 87-93.
Gomez et al., "Hydrogen production: two stage processes for waste degradation", Bioresource Technology, Sep. 1, 2011, vol. 102, No. 18, pp. 8621-8627.
Guo et al., "Enhancement of butanol production and reducing power using a two-stage controlled-pH strategy in batch culture of Clostridium acetobutylicum XY16", World Journal of Microbiology and Biotechnology, Jul. 2012, vol. 28, Issue 7, pp. 2551-2558.
Hafez, "Two-stage Anaerobic Digestion Process for H2 and CH4 Production from High Strength Industrial Organic Streams", Canadian Biogas Conference [online], May 2013, retrieved from Internet http://www.gtmconference.ca/site/index.php120 14-presentationsldoc down load3-9d1451-20 130b3d-hafez>, 13 pages.
Hafez, et al., "Effect of organic loading on a novel hydrogen bioreactor", International Journal of Hydrogen Energy, 2010, available online Nov. 10, 2009, vol. 35, pp. 81-92.
Hawkes et al., "Continuous dark fermentative hydrogen production by mesophilic microflora: Principles and progress", International Journal of Hydrogen Energy, 2007, available online Sep. 20, 2006, vol. 32 pp. 172-184.
Hawkes et al., "Sustainable fermentative hydrogen production: challenges for process optimisation", International Journal of Hydrogen Energy, Jan. 2002; 27, pp. 1339-1347.
Hisham Hafez et al., "Biological Hydrogen Production From Corn-Syrup Waste Using a Novel System," Energies (2009), Jun. 24, 2009, vol. 2, pp. 445-455.
Horiuchi, "Selective production of organic acids in anaerobic acid reactor by pH control", Bioresource Technology, May 2002, vol. 82, pp. 209-213.
Hussy et al., "Continuous fermentative hydrogen production from sucrose and sugarbeet", International Journal of Hydrogen Energy 2005, available online Jun. 15, 2004, 30, pp. 471-483.

(56) References Cited

OTHER PUBLICATIONS

International Preliminary Report on Patentability for Application No. PCT/CA2013/050121, dated Mar. 3, 2014, 10 pages.
International Preliminary Report on Patentability for Application No. PCT/CA2014/000600, dated Nov. 20, 2015, 19 pages.
International Preliminary Report on Patentability for Application No. PCT/CA2014/051011, dated Apr. 26, 2016, 8 pages.
International Search Report and Written Opinion for Application No. PCT/CA2013/050121, dated Apr. 18, 2013, 10 pages.
International Search Report for Application No. PCT/CA2014/000600, dated Oct. 17, 2014, 4 pages.
International Search Report for Application No. PCT/CA2014/051011, dated Jan. 16, 2015, 3 pages.
Jackson et al., "Anaerobic microbial metabolism can proceed close to thermodynamic limits", Nature Jan. 24, 2002, vol. 415, pp. 454-456.
Kim et al. , "Effect of gas sparging on continuous fermentative hydrogen production", International Journal of Hydrogen Energy, Mar. 29, 2006, 31, pp. 2158-2169.
Kraemer et al., "Improving the yield from fermentative hydrogen production", Biotechnol Lett, 2007, published online Feb. 6, 2007; 29, pp. 685-695.
Lalaurette et al., "Hydrogen production from cellulose in a two-stage process combining fermentation and electrohydrogenesis", International Journal of Hydrogen Energy, Aug. 2009, vol. 34 (15), pp. 6201-6210, XP026375050,ISSN: 0360-3199,[retrieved on Jun. 28, 2009].
Lee et al., "Biological hydrogen production: prospects and challenges", Trends Biotechnology, May 1, 2010, vol. 28, No. 5, pp. 262-271.
Levin et al., "Biohydrogen production: prospects and limitations to practical application", International Journal of Hydrogen Energy, vol. 29, issue 2, Feb. 2004, pp. 173-185.
Li et al.' "Fermentative Hydrogen Production from Wastewater and Solid Wastes by Mixed Cultures", Critical Reviews in Environmental Science and Technology, Jan. 12, 2007, vol. 37, No. 1, pp. 1-39.
Liang et al., "Behavioral study on hydrogen fermentation reactor installed with silicone rubber membrane", International Journal of Hydrogen Energy, vol. 27, Nov.-Dec. 2002, pp. 1157-1165.
Liu et al., "Electrochemically Assisted Microbial Production of Hydrogen from Acetate", Environmental Science & Technology, Apr. 22, 2005, vol. 39, No. 11, pp. 4317-4320.
Lu et al., "Hydrogen production with effluent from an ethanol-H2-coproducing fermentation reactor using a single-chamber microbial electrolysis cell", Biosensors and Bioelectronics, Jun. 2009, vol. 24 (10), pp. 3055-3060, XP026119043,ISSN: 0956-5663.
Mandal et al., "Improvement of biohydrogen production under decreased partial pressure of H2 by Enterobacter cloacae", Biotechnol Lett, Jun. 2, 2006, vol. 28, pp. 831-835.
Matsunaga et al., "Microaerobic Hydrogen Production by Photosythetic Bacteria in a Double-Phase Photobioreactor", Biotechnology and Bioengineering, Jun. 20, 2000, vol. 68, No. 6, pp. 647-651.
Nasr, "CO2 Sequestration: Effect on biohydrogen production and microbial community in the integrated biohydrogen reactor clarifier system (IBRCS)", Advanced Biofuels Symposium Poster Session Project No. 75, Ottawa Ontario May 27-29, 2014, retrieved from the internet: http://www.biofuelnetca/wp-conlentluploads120 14/05/roster-session Abstracts.pdf, 2 pages.

Nath et al., "Improvement of fermentative hydrogen production: various approaches", Appl Microbiol Biotechnol, Jul. 31, 2004, 65, pp. 520-529.
O-Thong et al., "Evaluation of methods for preparing hydrogen-producing seed inocula under thermophilic condition by process performance and microbial community analysis", Bioresource Technology, vol. 100, 2009, available online Sep. 2, 2008, pp. 909-918.
Park et al., "Removal of Headspace CO2 Increases Biological Hydrogen Production", Environmental Science & Technology, May 5, 2005, vol. 39, No. 12, pp. 4416-4420.
Rozendal et al., "Principle and perspectives of hydrogen production through biocatalyzed electrolysis", International Journal of Hydrogen Energy, Feb. 2006, vol. 31, pp. 1632-1640.
Show et al., "Critical assessment of anaerobic processes for continuous biohydrogen production from organic wastewater", International Journal of Hydrogen Energy, vol. 35, issue 24, Available online Dec. 29, 2009, pp. 13350-13355.
Show et al., "Production of hydrogen in a granular sludge-based anaerobic continuous stirred tank reactor", International Journal of Hydrogen Energy, Aug. 27, 2007; 32, pp. 4744-4753.
Supplementary European Search Report for Application No. EP13749197, dated Aug. 31, 2015, 7 Pages.
Tanisho et al., "Effect of CO2 Removal on Hydrogen Production by Fermentation", International Journal of Hydrogen Energy, vol. 23, No. 7, Jul. 1998 pp. 559-563.
U.S. Appl. No. 13/768,449, Office Action dated Sep. 16, 2015.
U.S. Appl. No. 14/518,307, Office Action dated Feb. 23, 2016.
U.S. Appl. No. 14/518,307, Office Action dated Sep. 4, 2015.
Vallero et al., "High rate sulfate reduction in a submerged anaerobic membrane bioreactor (SAMBaR) at high salinity", Journal of Membrane Science, May 5, 2005, vol. 253, pp. 217-232.
Vavilin et al., "Modelling Hydrogen Partial Pressure Change as a Result of Competition Between the Butyric and Propionic Groups of Acidogenic Bacteria", Bioresource Technology, accepted for publication Aug. 26, 1995, 54, pp. 171-177.
Villano, M. et al., "Perspectives of biofuels production from renewable resources with bioelectrochemical systems", Asia-Pacifc Journal of Chemical Engineering, Aug. 1, 2012, vol. 7, No. Suppl. 3, pp. S263-S274.
Guo et al., "Enhancement of Butanol Production and Reducing Power Using a Two-stage Controlled-ph Strategy in Batch Culture of Clostridium Acetobutylicum XY16," World Journal of Microbiology and Biotechnology, Jul. 2012, vol. 28 (7), pp. 2551-2558.
U.S. Appl. No. 14/907,475, Notice of Allowance dated Mar. 29, 2017.
European Patent Application No. 14829514, Supplementary European Search Report dated Feb. 27, 2017.
European Patent Application No. 14855028.8, Extented European Search Report dated Apr. 25, 2017.
Hazef et al., "Biological Hydrogen Production from Corn-Syrup Waste Using a Novel System," Energies,Jun. 24, 2009, vol. 2(2), pp. 445-455.
U.S. Appl. No. 14/518,307, Office Action dated Oct. 12, 2016.
Vavilin et al., "Methanosarcina as the Dominant Aceticlastic Methanogens During Mesophilic Anaerobic Digestion of Putrescible Waste", Antonie van Leeuwenhoek, Nov. 2008, vol. 94 (4), pp. 593-605.
Indian Patent Application No. 7590/DELNP/2014, Office Action dated Apr. 24, 2018.

* cited by examiner

METHOD AND SYSTEM FOR ELECTRO-ASSISTED HYDROGEN PRODUCTION FROM ORGANIC MATERIAL

CROSS REFERENCE TO RELATED APPLICATIONS

This application is a divisional of U.S. Continuation patent application Ser. No. 13/768,449 filed on Feb. 15, 2013, now U.S. Pat. No. 9,458,474 entitled METHOD AND SYSTEM FOR ELECTRO-ASSISTED HYDROGEN PRODUCTION FROM ORGANIC MATERIAL, which claims priority from U.S. Provisional Application Ser. No. 61/600,325, filed Feb. 17, 2012 and entitled ELECTRO-ASSISTED BIOHYDROGENATOR FOR HYDROGEN PRODUCTION FROM ORGANIC WASTE, the contents of which are hereby incorporated by reference.

FIELD

The present disclosure relates to production of hydrogen. More particularly, the present disclosure relates to the treatment of organic material with microorganisms for the production of hydrogen.

BACKGROUND

The problems of soaring energy demand and environmental pollution are addressed by various biological processes for the treatment of industrial wastes. Biohydrogen production through dark fermentation is one known process for the treatment of industrial waste for the production of hydrogen.

Microorganisms are capable of producing hydrogen via either photosynthesis or preferably through fermentation (Matsunaga, T., Hatano, T., Yamada, A., Matsumoto, M., (2000) Microaerobic hydrogen production by photosythetic bacteria in a double phase photobioreactor. *Biotechnol. Bioeng.* 68 (6), 647-651). Organic pollutants are anaerobically converted to methane in two distinct stages: acidification and methanogenesis. Acidification produces hydrogen as a by-product which in turn is used as an electron donor by many methanogens at the second stage of the process (Fang, H. H. P. and Liu, H. (2002) Effect of pH on hydrogen production from glucose by a mixed culture. *Bioresource Technology* 82, 87-93). Separation of the two stages is feasible for hydrogen collection from the first stage. The second stage is further used for treatment of the remaining acidification products, which includes mainly volatile fatty acids (VFAs).

The continuously stirred tank reactor (CSTR) has been the most widely used system for continuous hydrogen production (Li, C., Fang, H. H. P., (2007) Fermentative hydrogen production from wastewater and solid wastes by mixed cultures. *Critical reviews in Env. Sci. and Tech.*, 37, 1-39). Since in a CSTR biomass solids residence time (SRT) is the same as the hydraulic retention time (HRT), its concentration in the mixed liquor is highly affected by the recommended HRT of 1-12 h which is optimal for high hydrogen production rates (Li and Fang, 2007). The maximum specific growth rate ($\mu$max) for mixed culture of 0.333 h−1 (Horiuchi J. I., Shimizu T., Tada K., Kanno T., Kobayashi M., (2002) Selective production of organic acids in anaerobic acid reactor by pH control. *Bioresource Technol* 82, 209-13) corresponds to an SRTmin of 3.0 h.

However, high dilution rates result in a marked decrease in biomass content in the reactor due to severe cell washout and system failure (Wu, S. Y., Hung, C. H., Lin, C. Y., Lin, P. J., Lee, K. S., Lin, C. N., Chang, F. Y. And Chang, J. S. (2008) HRT-dependent hydrogen production and bacterial community structure of mixed anaerobic microflora in suspended, granular and immobilized sludge systems using glucose as the carbon substrate. *Int. J. Hydrogen Energy* 33, 1542-1549). Since Acetone-butanol-ethanol (ABE) fermentation utilizes the same bacterial groups that are used for biohydrogen, the process also suffers from biomass washout. Therefore, to resolve biomass washout in ABE fermentation, most of studies in the literature and full-scale applications have utilized batch or fed-batch reactors.

Decoupling of SRT from HRT in hydrogen bioreactors has been achieved primarily by using biofilms on several media including synthetic plastic media and treated anaerobic granular sludge (Das, D., Khanna, N., Veziroglu, T. N., (2008) Recent developments in biological hydrogen production processes. *Chem Ind. And chem.* Eng. 14 (2), 57-67), activated carbon, expanded clay and loofah sponge (Chang, J. S., Lee, K. S., and Lin, P. J., (2002) Biohydrogen production with fixed-bed bioreactors. *Int. J. Hydrogen Energy* 27 (11/12), 1167-1174), glass beads (Zhang, H., Mary, A. B., Bruce, E. L., (2006) Biological hydrogen production by *clostridium acetobutylicum* in an unsaturated flow reactor. *Water Research* 40, 728-734) and membranes (Vallero, M. V. G., Lettinga, G., and Lens, P. N. L., (2005) High rate sulfate reduction in a submerged anaerobic membrane bioreactor (SAMBaR) at high alinity. *J. Membr. Sci.* 253(1/2), 217-232). Problems with the development of methanogenic biofilms on the carrier media adversely impact process stability, which is critical for sustained hydrogen production. Moreover, membranes have not shown many advantages in terms of volumetric hydrogen yield and are also prone to fouling in such a reductive environment.

A biohydrogenator system provided in WO2010/085893 is intended to address two limitations for sustained biological hydrogen production: contamination of the microbial hydrogen-producing cultures with methane-producing cultures and low bacterial yield of hydrogen-producers. In that system, a gravity settler is used after a hydrogen reactor for decoupling SRT from HRT through sludge. The system disclosed includes a CSTR for biological hydrogen production, followed by a gravity settler positioned downstream of the CSTR, the combination of which forms the biohydrogenator. The biomass concentration in the hydrogen reactor is kept at the desired range through biomass recirculation from the bottom of the gravity settler and/or biomass wastage from the gravity settler's underflow. This prior art biohydrogenator is described to increase hydrogen yield from sugar and carbohydrate based wastes from 1.6 to 3.2 mol $H_2$/mol glucose while producing VFAs primarily acetate as the residual soluble metabolite. Although that represents an improvement over previous systems, this biohydrogenator is still subject to the limitations common to dark fermentation processes: the inhibition of hydrogen production by the accumulation of fermentation end-products. The production and accumulation of acetic and butyric acids results in lower hydrogen yields and a total undissociated acid concentration of 19 mM initiated solventogenesis. Different strains of *Clostridium* produce different ratios of end-products thus affecting their hydrogen-producing potential. The elimination of butyric acid formation and the increased production of acetic acid would provide for increased hydrogen yield from glucose. Although acetate production would increase hydrogen yield to 4 mol of hydrogen per mole of glucose, this is still not enough for the process to be an economically viable alternative to existing hydrogen production methods.

Another biohydrogen production process is the electrohydrogenesis process. In an electrogenesis process, exoelectrogenic bacteria are able to release electrons exogeneously (outside the cell) to solid substrates (i.e. a carbon electrode), allowing electricity to be produced in a reactor called a microbial fuel cell (MFC). The oxidation reaction generated by the bacteria at the anode is sustained through the production of water at the cathode from electrons and protons released by the bacteria, and oxygen. The electrohydrogenesis process is similar except that a small potential must be added into the circuit and no oxygen is used at the cathode. Thus, hydrogen gas is evolved at the cathode in a reactor called a microbial electrolysis cell (MEC). The process has also been referred to as a bacterial electrolysis cell (BEC) and a bioelectrochemically assisted microbial reactor (BEAMR): Liu, H., Grot, S., Logan, B. E., (2005) Electrochemically assisted microbial production of hydrogen from acetate. *Environ. Sci. Technol.*, 39, 4317-4320; Rozendal, R. A., Buisman, C. J. N., Bio-Electrochemical Process for Producing Hydrogen. International Publication No. WO 2005/005981; and Rozendal, R. A., Hamelers, H. V. M., Euverink, G. J. W., Metz, S. J.; Buisman, C. J. N. (2006), Principle and perspectives of hydrogen production through biocatalyzed electrolysis. *Int. J. Hydrogen Energy*, 31, 1632-1640. The BEAMR process differs from MFC with respect to loss of hydrogen due to its diffusion from the cathode chamber through the cation exchange membrane (CEM) into the anode chamber. In addition, in the BEAMR process there is no potential for loss of substrate resulting from aerobic growth of bacteria due to oxygen diffusion into the anode chamber from the cathode chamber.

All of these known electrohydrogenesis processes are coupled with, and in fact dependent on, an upstream dark fermentation process (i.e. two completely separate process stages). The advantages of a separate electrohydrogenesis process were evaluated in Liu et al. (2005), Rozendal & Buisman (2005), and Rozendal et al. (2006).

The most widely reported problems with dark fermentation reactors in the literature were microbial shifts, metabolic shifts, biomass washouts, repeated systems failure, sustainability, low hydrogen yields, methanogens growth and methane production as opposed to hydrogen. With all the aforementioned problems, researchers have moved on to the MEC microbial electrolysis cells and assumed that in the future a sustainable dark fermentation process can be used upstream of the MEC for acids production in dark fermentation to be utilized in the MEC. Again with the MEC, researchers have reported several problems due to their reactor configurations i.e. high hydrogen yields requires short retention time in the MEC while the microorganisms tend to escape at high dilution rates thus researchers always use long retention times in the MECs in an attempt to mitigate biomass washout, but extending retention times lead to the growth of methanogens, a group of microorganisms which consumes hydrogen and produces methane. Thus, an improved process is desired which would address at least some of these problems.

SUMMARY

The present disclosure provides a hydrogen generation process and system which respectively include and facilitate application of two processes for hydrogen production from organic material (for example industrial organic waste and biomass): dark fermentation and electro-assisted fermentation. Both dark fermentation and electro-assisted fermentation are applied in a single bioreactor. The process and system disclosed herein mitigate at least one of the above disadvantages with prior art dark fermentation and electrohydrogenesis processes. In addition to hydrogen gas, the process and system are also applicable to production of other chemicals, including acetone, butanol, ethanol, acetic acid, butyric acid.

Previously, since the dark fermentation and electrohydrogenesis processes use different organisms and conditions, these processes were coupled sequentially to avoid interference between the processes. It has now been surprisingly discovered that not only can an electrohydrogenesis process be operated within the dark fermentation broth without a significant negative effect on either process, combining the processes also provides some unexpected advantages.

The electrobiohydrogenation process and system herein disclosed may result in consumption of acids formed during the dark fermentation process, and a corresponding decrease in the amount of buffer (e.g. sodium bicarbonate) required to maintain the dark fermentation pH at a desirable range (e.g. from 5.5 to 6.8). Moreover, by integrating the dark fermentation and electrohydrogenesis processes, continuous conversion and removal of the acetate, butyrate, propionate, valerate, and other volatile fatty acids (VFAs) produced as a by-products in dark fermentation is achieved, which may result in both lower fermentation inhibition by fermentation end products and increased yield of $H_2$.

Dark fermentation is a conversion process wherein a reduction in chemical oxygen demand (COD) of about 30% can be achieved (formation of VFAs constitutes 70% of the COD). In order to increase yields to 8-9 mol of hydrogen per mole glucose, acetate that is produced as a by-product is converted to $H_2$ by electrohydrogenesis operated simultaneously in the electrobiohydrogenator. This may result in improved decreases in COD, and possibly up to about 90% removal of COD. The electrobiohydrogenator may also mitigate biomass washout (a problem associated with MECs) by separation of solids from liquids in a gravity settler, resulting in decoupling of solids retention time (SRT) from hydraulic retention time (HRT) and allowing recirculation from the gravity setter to the bioreactor, facilitating operation at greater biomass concentrations and with lower retention times.

In a first aspect, the present disclosure provides a method for producing hydrogen from organic material, including providing organic material and hydrogen-producing microorganisms into a completely mixed bioreactor for breaking down the organic material into products including $H_2$, $CO_2$, fatty acids, and alcohols; recovering at least a portion of the $H_2$ and of the $CO_2$ from the completely mixed bioreactor; recovering at least a portion of a first liquid effluent from the completely mixed bioreactor, the first liquid effluent including at least a portion of the hydrogen-producing microorganisms, the fatty acids, and of the alcohols; providing at least a portion of the first liquid effluent into a gravity settler for separating at least a portion of the first liquid effluent into a concentrated biomass including at least a portion of the hydrogen-producing microorganisms and a second liquid effluent including at least a portion of the fatty acids and the alcohols; recovering at least a portion of the concentrated biomass from the gravity settler and providing the concentrated biomass into the completely mixed bioreactor; and applying an input voltage to at least one of the completely mixed bioreactor and the gravity settler for facilitating an electrohydrogenesis process therein.

In an embodiment, applying the input voltage includes applying the input voltage to the completely mixed bioreactor.

In an embodiment, the method includes recovering at least a portion of the $H_2$ and of the $CO_2$ from the gravity settler. In an embodiment, applying the input voltage includes applying the input voltage to the gravity settler, and the method includes recovering at least a portion of $H_2$ and $CO_2$ produced by electrohydrogenesis in the gravity settler. In an embodiment, the temperature in the gravity settler is maintained at between about 20° C. and about 70° C.

In an embodiment, the temperature in the completely mixed bioreactor is maintained at between about 20° C. and about 70° C.

In an embodiment, the input voltage is between about 0.5 V and about 1.8 V. In an embodiment, the input voltage is about 1.0 V.

In an embodiment, the input voltage is a continuous voltage.

In an embodiment, the input voltage is an intermittent voltage.

In an embodiment, the method includes providing the second liquid effluent into a biomethanator for production of methane from the second liquid effluent. In an embodiment, the method further includes providing the second liquid effluent into a storage tank prior to providing the second liquid effluent into the biomethanator. In an embodiment, the temperature in the biomethanator is maintained at between about 20° C. and about 70° C.

In an embodiment, the hydrogen producing microorganisms include one or more of the species selected from the group consisting of C. acetobutyricum, B. thuringiensis, and C. butyricum.

In a second aspect, the present disclosure provides an electrobiohydrogenator system for producing hydrogen from organic material, including a completely mixed bioreactor for microorganism-mediated breakdown of the organic material into products including $H_2$, $CO_2$, fatty acids, and alcohols, a gravity settler hydraulically connected to the completely mixed bioreactor for receiving at least a portion of a first liquid effluent from the completely mixed bioreactor, and at least one pair of electrodes for applying an input voltage to at least one of the completely mixed bioreactor and the gravity settler for facilitating an electrohydrogenesis process. The bioreactor includes an inlet for receiving the organic material; a first outlet for recovering at least a portion of the $H_2$ and of the $CO_2$ from the completely mixed bioreactor; and a second outlet for recovering at least a portion of a first liquid effluent from the completely mixed bioreactor, the first liquid effluent including at least a portion of the hydrogen-producing microorganisms, the fatty acids, and of the alcohols. The gravity settler includes a settling container for separating at least a portion of the first liquid effluent into a concentrated biomass including at least a portion of the hydrogen-producing microorganisms and a second liquid effluent including at least a portion of the fatty acids and the alcohols; and a third outlet hydraulically connected to the settling container and located at a lower portion of the settling container for recovering at least a portion of the concentrated biomass from the gravity settler and providing the concentrated biomass into the completely mixed bioreactor.

In an embodiment, the pair of electrodes is for applying the input voltage to the completely mixed bioreactor.

In an embodiment, the gravity settler includes a fourth outlet for recovering at least a portion of the $H_2$ and of the $CO_2$ from the gravity settler. In an embodiment, the pair of electrodes is for applying the input voltage to the gravity settler. In an embodiment, the system includes a first temperature controller for maintaining the temperature in the gravity settler at between about 20° C. and about 70° C.

In an embodiment, the system includes a second temperature controller for maintaining the temperature in the completely mixed bioreactor at between about 20° C. and about 70° C.

In an embodiment, the gravity settler further includes a fifth outlet for discharging the second liquid effluent from the gravity settler. In an embodiment, the system includes a biomethanator hydraulically connected to the fifth outlet for facilitating production of methane from the second liquid effluent. In an embodiment, the system includes a storage tank hydraulically connected to the fifth outlet and the biomethanator, and intermediate the fifth outlet and the biomethanator, for receiving the second liquid effluent from the gravity settler. In an embodiment, the system includes a third temperature controller for maintaining the temperature in the biomethanator at between about 20° C. and about 70° C.

DETAILED DESCRIPTION

The process and system herein provided involve application of two processes for hydrogen production and treatment of waste: dark fermentation and electro-assisted fermentation. The process and system herein provided are directed to mitigating some drawbacks of previous techniques for sustained biological hydrogen production: contamination of microbial hydrogen-producing cultures with methane-producing cultures (sometimes necessitating frequent re-start-up or other methanogenic bacteria inactivation techniques), low bacterial yield of hydrogen-producers culminating in microbial washout from the system and failure, and a maximum hydrogen yield of 3.2 mol $H_2$/mol glucose reported for dark fermentation out of the theoretical maximum of 12 mol $H_2$/mol glucose.

In Liu et al. (2005), it was postulated that based on dark fermentation and electrohydrogenesis processes, the overall hydrogen yield can be as high as 8-9 mol $H_2$/mol hexose, although they verified experimentally and in batch studies only that 1 mole of acetate can produce as much as 2.9 moles of hydrogen using electrohydrogenesis. Thus it has not been proven experimentally using continuous flow systems that a single bioreactor process of simultaneous dark fermentation and electrohydrogenesis could be successfully operated, nor whether 8-9 mol H₂/mol glucose can be sustained in such a single bioreactor process.

Interpretation

As used herein, the term "about", when used in conjunction with ranges of dimensions, concentrations, temperatures or other physical or chemical properties or characteristics is meant to cover slight variations that may exist in the upper and lower limits of the ranges of properties or characteristics.

As used herein, the phrases "completely mixed bioreactor" or "continuously stirred tank reactor" (CSTR) mean a mechanically or hydraulically agitated vessel including microorganisms in suspension and a growth media, typically including nutrients such as organic carbon, nitrogen-containing compounds, phosphorous-containing compounds, and trace mineral solutions.

As used herein, the phrase "hydrogen producing microorganisms" means microorganisms capable of fermenting organics under anaerobic conditions to produce hydrogen, carbon dioxide, and a variety of organic acids and alcohols.

As used herein, the phrase "organic waste" refers to wastes that include carbon and hydrogen such as, but are not limited to, alcohols, ketones aldehydes, VFAs, esters, carboxylic acids, ethers, carbohydrates, proteins, lipids, polysaccharides, monosaccharide, cellulose, and nucleic acids. Organic waste may originate, for example, from high strength industrial waste waters, such as those commonly associated with the food and agriculture sector, bioethanol industries, and young landfill leachates from non-hazardous waste disposal sites.

As used herein, the terms "comprises", "comprising", "includes" and "including" are to be construed as being inclusive and open ended, and not exclusive. Specifically, when used in this specification including claims, the terms "comprises", "comprising", "includes" and "including" and variations thereof mean the specified features, steps or components are included. These terms are not to be interpreted to exclude the presence of other features, steps or components.

Electrobiohydrogenator System and Electrobiohydrogenation Process

Figure 1:
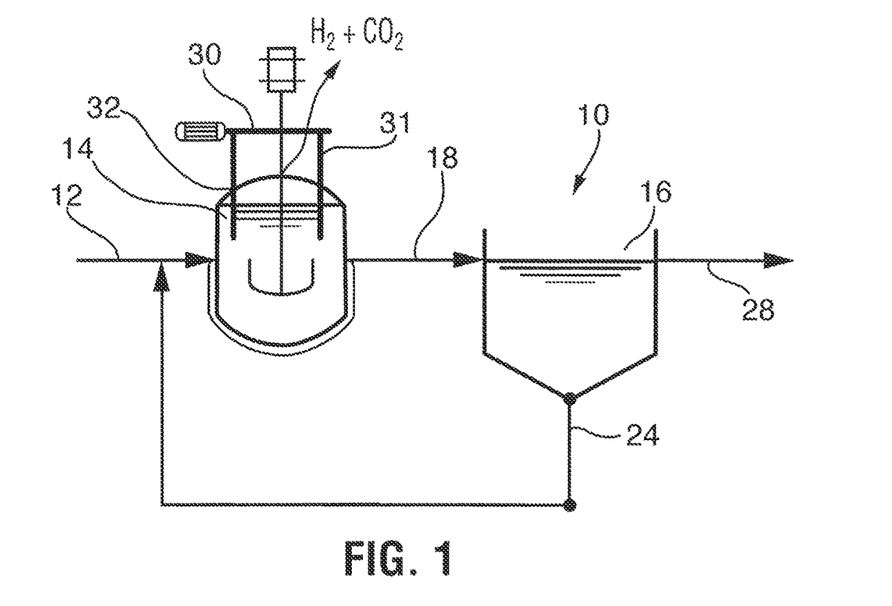
FIG. 1 is a schematic illustration of an electrobiohydrogenator reactor and gravity settler.

Referring to FIG. 1, an electrobiohydrogenator system 10 for producing hydrogen and methane from organic waste in an electrobiohydrogenation process is shown. The system 10 includes a completely mixed bioreactor 14 (e.g. a CSTR) having an input for receiving organic material 12 (e.g. organic waste) into the completely mixed bioreactor 14. A gravity settler 16 (also referred to as a clarifier) is located downstream of the completely mixed bioreactor 14 and hydraulically connected with an outlet of the completely mixed bioreactor 14 for receiving a first effluent 18 from the completely mixed bioreactor 14. The system 10 includes hydrogen producing microorganisms located in the completely mixed bioreactor 14 for breaking down the organic material 12.

A lower portion of the gravity settler 16 is hydraulically connected to the completely mixed bioreactor 14 for recirculating settled biomass 24 from the gravity settler 16 to the completely mixed bioreactor 14 (for example through a feedback conduit). For example, the settled biomass 24 may be mixed with the organic material 12 being provided to the completely mixed bioreactor 14. Recirculation of settled biomass 24 from the gravity settler 16 to the completely mixed bioreactor 14 maintains the biomass concentration at the desired range.

When dark fermentation is carried out, glucose may be converted to H₂, CO₂, and either acetate or butyrate by the reactions shown below in equations (1) and (2), respectively:

(1)

(2)

The acetate and butyrate may then in turn each be converted into further H₂ and CO₂ by the reactions shown below in equations (3) and (4):

(3)

(4)

An external voltage may be applied for overcoming the positive ΔG values associated with the reactions of equations 3 and 4 (and making the ΔG values associated with the reactions of equations 1 and 2 more negative). For example, a voltage of between about 0.5 V and about 1.8 V may be applied depending on many factors (e.g. desired products formation, external and internal resistance of the system, etc.).

Figure 2:
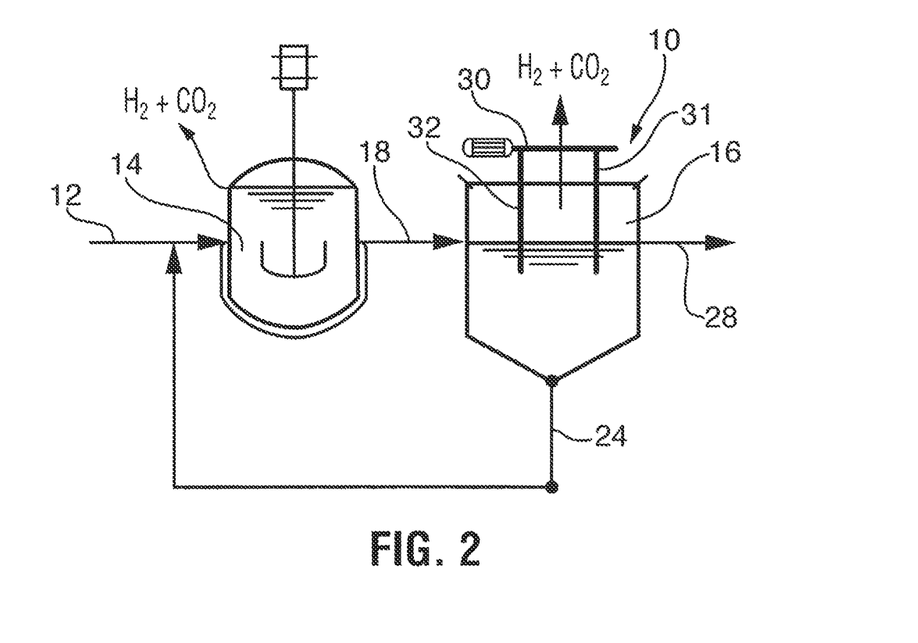
FIG. 2 is a schematic illustration of an biohydrogenator reactor and electro-assisted gravity settler.

In addition to the completely mixed bioreactor 14 for biological hydrogen production and the gravity settler 16, the system 10 includes an electrode arrangement 30 for the application of an input voltage. The electrode arrangement 30 includes an anode 31 and cathode 32. The electrode arrangement 30 may be placed at one or more of two alternative locations in the system 10. In FIG. 1, the electrode arrangement 30 is placed in the continuously mixed bioreactor 14 (providing an electrobiohydrogenator reactor). In FIG. 2, the electrode arrangement 30 is placed in the gravity settler 16 (providing an electro-assisted gravity settler). The gravity settler 16 of FIG. 2, which includes the electrode arrangement 30, is a covered gravity settler for facilitating recovery of the H₂ and CO₂ produced in the gravity settler 16. VFAs are present in both the completely mixed bioreactor 14 and the gravity settler 16, and are the main soluble metabolites in the gravity settler 16. Integration of the electro-assisted process into the system 10 is accomplished by submerging the electrode arrangement 30 in the continuously mixed bioreactor 14 (FIG. 1), the gravity settler 16 (FIG. 2), or both (not shown), and supplying an input voltage. The input voltage may be continuous, intermittent, or both. The electrode material can be, for example, platinum, graphite, or stainless steel. The voltage at pH 7 required to produce hydrogen is theoretically −0.61 V (Vcat versus Ag/AgCl). The anode potential produced by the bacterial oxidation of the organic matter is about −0.50 V (Van), so the minimum theoretical applied voltage is 0.11 V (Vapp=Van−Vcat). In practice, the minimum applied voltage to produce hydrogen from the bioelectrolysis of acetate has been found to be more than 0.25 V due to ohmic resistance and electrode overpotential, which is still substantially less than the 1.8-2.0 V needed for hydrogen production via water electrolysis (alkaline conditions).

The method and system may be practiced with varying schedules of operation with respect to applying power to the electrode arrangement 30. For example, the frequency of power application cycles may be adjusted to apply the method and operate the system on a 24 hour schedule.

Hydrogen gas (H₂), carbon dioxide (CO₂), and the first effluent 18, are emitted from the completely mixed bioreactor 14. The first liquid effluent 18 includes VFAs, primary alcohols and hydrogen-producing microorganisms. The H₂ and $CO_2$ are recovered. The first liquid effluent 18 flows to the gravity settler 16. The hydrogen producing microorganisms settle to the bottom of, and are concentrated in, the gravity settler 16. The settled hydrogen-producing microorganisms in the bottom of the gravity settler 16 are recirculated back to the completely mixed bioreactor 14, leaving a second liquid effluent 28 in the gravity settler 16.

Figure 3:
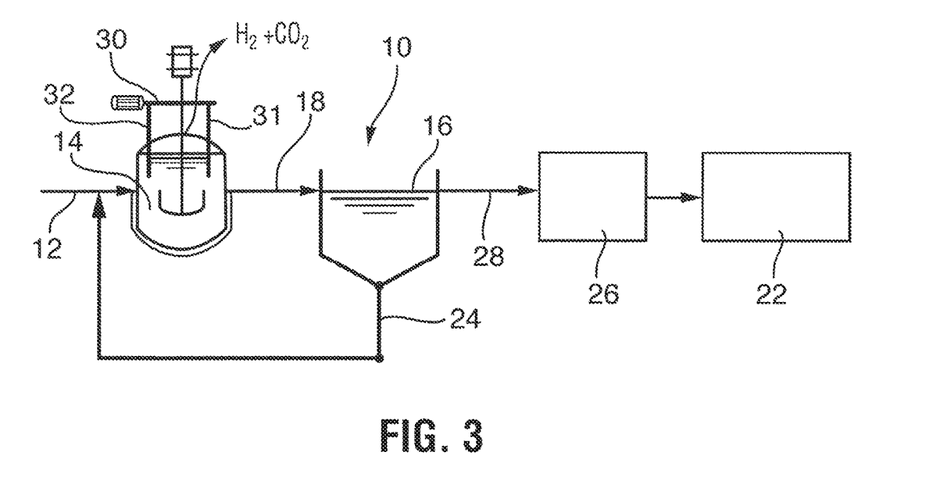
FIG. 3 is a schematic illustration of an electrobiohydrogenator reactor, gravity settler, storage tank, and biomethanator reactor.

FIG. 3 shows an embodiment of the system 10 including a biomethanator 22. The second liquid effluent 28 from the gravity settler 16 is loaded with residual VFAs that were not converted to hydrogen during power application in either or both configurations of the electrode arrangement 30 (e.g. electrobiohydrogenator reactor and gravity settler, biohydrogenator reactor and electro-assisted gravity settler, or electrobiohydrogenator reactor and electro-assisted gravity settler) as a result of microbiological breakdown of the influent waste constituents by hydrogen-producing bacteria, and is an excellent substrate for methane-forming bacteria. Thus, the second effluent 28 can advantageously be directed to the biomethanator 22. Production of VFAs in the completely mixed bioreactor 14 may improve the efficiency of the second-stage biomethanator 22, for example by increasing the volumetric methane production rate, methane yield, or solids destruction efficiency, thus allowing for higher volumetric and organic loading rates. It is expected that the aforementioned beneficial impact of the system 10 on this second-stage anaerobic treatment process is independent of the second-stage biomethanator 22 reactor design and/or configuration.

As also shown in FIG. 3, the system 10 may include a storage tank 26 hydraulically connected to and located downstream of, the gravity settler 16. The storage tank 26 may be located upstream of the optional biomethanator 22, and hydraulically connected to both the gravity settler 16 and biomethanator 22 for adjusting loading rates of the liquids entering the biomethanator 22.

The system 10 may include a dispenser (not shown) for dispensing chemicals into the storage tank 26 for adjusting alkalinity, pH, or other properties of the liquid in the storage tank 26. The system 10 may also include a dispenser (not shown) for dispensing nutrients and pH adjustment compounds into the completely mixed bioreactor 14. The nutrients may include any one or combination of: nitrogen containing compounds, phosphorous containing compounds and trace metals (including iron, manganese, magnesium, calcium, cobalt, zinc, nickel, and copper). The pH adjustment compounds may include soda ash, sodium bicarbonate, sodium hydroxide, calcium hydroxide, magnesium hydroxide, nitric acid, and hydrochloric acid.

Examples of hydrogen generating microorganisms include *C. acetobutyricum*, *B. thuringiensis*, and *C. butyricum*.

The system 10 may also include temperature controllers for controlling the temperature in the completely mixed bioreactor 14, in the biomethanator 22 or both. A typical temperature range in which the temperature of the contents of both the completely mixed bioreactor 14 and the biomethanator 22 is maintained may be from about 20° C. to about 70° C. Where the gravity settler 16 is an electro-assisted gravity settler (e.g. FIG. 2), the gravity settler 16 may include temperature controllers for controlling the temperature in the range of 20° C. to about 70° C.

Example I

A lab-scale conventional biohydrogenator was operated at 37° C. with an organic loading rate of 25.7 gCOD/L-d ("gCOD" is a measure of COD in grams). The biohydrogenator included a CSTR for biological hydrogen production (5 L working volume) hydraulically connected to an uncovered (i.e. open to atmosphere) gravity settler (volume 8 L) for the decoupling of SRT from HRT. The feed contained the following inorganics: 2000-16000 mg/L $NaHCO_3$; 140 mg/L $CaCl_2$; 160 mg/L $MgCl_2.6H_2O$; 600 mg/L $NH_4HCO_3$; 160 mg/L $MgSO_4.7H_2O$; 500-2000 mg/L urea, 124-300 mg/L $Na_2CO_3$; 156 mg/L $KHCO_3$; 15-20 mg/L $K_2HPO_4$; 500 mg/L trace mineral solution; and 250-1500 mg/L $H_3PO_4$.

At steady-state operation of the biohydrogenator, acetic and butyric acids were the predominant VFAs in the reactor, at concentrations of 2500 mg/L and 1600 mg/L, respectively. A hydrogen yield of 2.8 mol $H_2$/mol glucose was achieved at a hydrogen production rate of 10 L $H_2/L_{reactor}$/d.

The dark fermentation COD mass balance at steady-state operation including biomass yield can be written as follows:

8.56 gCOD (glucose)→2.675 gCOD (acetic acid)+ 2.896 gCOD (butyric acid)+1.905 gCOD (hydrogen)+1.08 gCOD (biomass)     (5)

It is expected that after the system reaches steady-state fermentation, the following reactions will occur, if an external voltage ranging from 0.5 V to 0.9 V is applied, assuming an efficiency of 75%:

2.675 gCOD (acetic acid)→2 gCOD (hydrogen)+ 0.461 gCOD (acetic acid)+0.214 gCOD (biomass)     (6)

2.896 gCOD (butyric acid)→2.172 gCOD (hydrogen)+0.494 gCOD (butyric acid)+0.23 gCOD (biomass)     (7)

Therefore, the expected overall process performance (dark fermentation+electro-assistance) can be predicted in the following COD mass balance equation:

8.56 gCOD (glucose)→6.07 gCOD (hydrogen)+ 0.461 gCOD (acetic acid)+0.494 gCOD (butyric acid)+1.524 gCOD (biomass)     (8)

It is expected that application of an external voltage of 0.5 V to 0.9 V will increase hydrogen yield by a factor of about 3. The energy required for the external voltage is equivalent to 1 to 1.5 mole hydrogen/mole glucose. Thus, the net hydrogen yield is expected to be 7 to 7.5 mole hydrogen/mole glucose. Consequently, since 1 electron is required for every molecule in 7, every 14 grams of $H_2$ produced requires $6.022 \times 10^{23}$ electrons (since 1 mol is $6.022 \times 10^{23}$ molecules and $H_2$ has a molar mass of about 2 g/mol).

Example II

Systems Set Up and Operations

A lab-scale system as shown in FIG. 1 was operated at 37° C. for 15 days, with an organic loading rate of 20 gCOD/L-d. The HRT was 8 hr and the SRT was estimated at 2.3 days. The system is an electro-assisted integrated biohydrogen reactor clarifier system, and included a CSTR for biological hydrogen production (5 L working volume) hydraulically connected to an uncovered (i.e. open to atmosphere) gravity settler (volume 8 L) for the decoupling of SRT from the HRT. In order to enrich hydrogen producing bacteria, prior to start-up, anaerobic digester sludge from the St. Marys wastewater treatment plant (St. Marys, Ontario, Canada) was heat treated in a baker at 70° C. for 30 minutes and was then used to seed the system. The system was monitored for COD, soluble COD, VFAs, ethanol, lactate, glucose, volatile suspended solids (VSS), total suspended solids and biogas composition including hydrogen, methane and nitrogen. The quantity of produced biogas was recorded using a wet tip gas meter (Rebel wet-tip gas meter company, Nashville, Tenn., USA).

Figure 4:
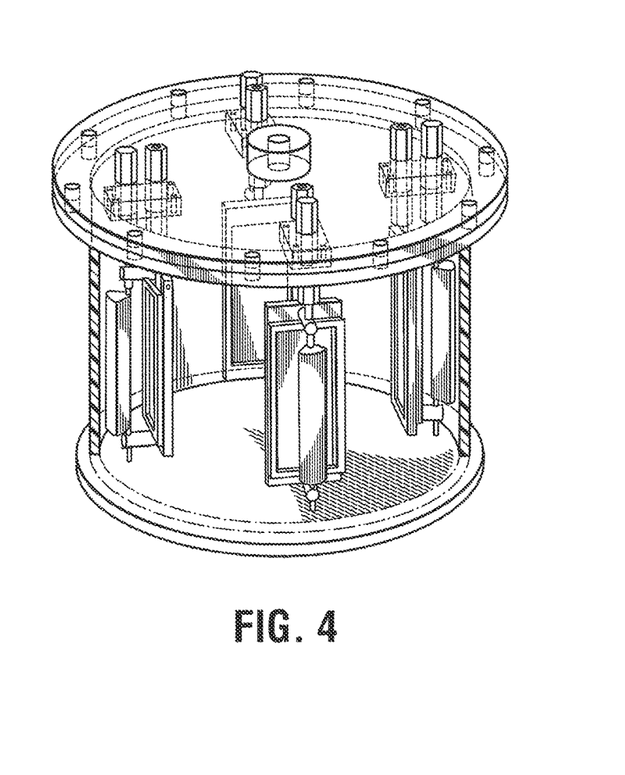
FIG. 4 is an embodiment of an electrode assembly and electrobiohydrogenator reactor of FIG. 1 or 3.

FIG. 4 shows the biohydrogen reactor used in the lab-scale system. The voltage was applied to the biohydrogen reactor through four pairs of electrodes. The anodes were made of graphite brushes (25 mm diameter×150 mm length; fiber type; Gordon Brush Mfg Co., Inc., Commerce, Calif.) removed on one side to form half cylinder with specific surface area of 71.7 $cm^2/cm^3$-brush volume. The cathodes were made of carbon cloth 40 wt % Pt/C (Fuel Cell Earth Co., Inc) and stainless steel 304 mesh (mesh size #40, McMaster-Carr) with specific surface area of 2.54 $cm^2/cm^2$ attached to each other forming a cathode of one side carbon cloth and the other stainless steel mesh. The active surface area of four cathodes in total was 308 $cm^2$ (3.5 $m^2/m^3$-reactor volume) for carbon cloth side and 914 $cm^2$ (10 $m^2/m^3$-reactor volume) for the side covered with stainless steel mesh. The distance between the cathode and the anode of each electrode pair was 3 cm. The distance between the centers of an electrode pair and the next electron pair was 12 cm. For each pair of electrodes, a voltage of 1.0 V was applied using four separate power supplies (model 1665; BK Presision, Inc.). Each power supply had two leads; the negative lead was connected to the cathode and the positive lead was serially linked to an external resistance of 10Ω and to the anode. The current was calculated using Ohm's law (I=V/R), where V is the voltage drop across the 10Ω resistor measured using a multimeter (model 2700; Keithley Instruments, Inc.). After 3 days from start-up, when steady hydrogen production was established, power was applied in batch mode operation (i.e. 4 hours/day, once a day). During power application all the feed, effluent, and recycle pumps were switched off.

Inocula and Media Compositions

Anaerobically-digested sludge from the St. Marys wastewater treatment plant was used as the seed. The system was seeded with 5 liters of sludge and started up in a continuous dark fermentation mode for 4 days without power application. The feed contained 8 g/L of glucose and the following inorganics: 2000-4000 mg/L $NaHCO_3$; 140 mg/L $CaCl2$; 160 mg/L $MgCl_2.6H_2O$; 600 mg/L $NH_4HCO_3$; 160 mg/L $MgSO_4.7H_2O$; 500-2000 mg/L urea; 124-300 mg/L $Na_2CO_3$; 156 mg/L $KHCO_3$; 15-20 mg/L $K_2HPO_4$; 500 mg/L trace mineral solution; and 250-1500 mg/L $H_3PO_4$.

Analytical Methods

The biogas composition including $H_2$, $CH_4$, and $N_2$ was determined by a gas chromatograph (Model 310, SRI Instruments, Torrance, Calif.) equipped with a thermal conductivity detector (TCD) and a molecular sieve column (Molesieve 5A, mesh 80/100, 6 ft×⅛ in). Argon was used as carrier gas at a flow rate of 30 mL/min. The temperatures of the column and the TCD detector were 90° C. and 105° C., respectively. The concentrations of VFAs were analyzed using a gas chromatograph (Varian 8500, Varian Inc., Toronto, Canada) with a flame ionization detector equipped with a fused silica column (30 m×0.32 mm). Helium was used as carrier gas at a flow rate of 5 mL/min. The temperatures of the column and detector were 110° C. and 250° C., respectively. Lactic acid concentrations were measured using a high-performance liquid chromatography system (1200 series, Agilent Technologies) equipped with Aminex HPX-87H ion exclusion column (300 mm×7.8 mm I.D.; BIO-RAD), and a UV-detector at 210 nm. The column temperature was adjusted to 30° C. The same instrument with a refractive index detector (RID) was used to measure the concentrations of glucose. The temperature of the RID detector was set to 35° C. The amount of VSS and COD were measured according to standard methods.

System Performance During Dark Fermentation Mode

Steady-state was observed after 3 days from startup. The systems showed stable hydrogen production during the 30 days of operation. The coefficient of variation (calculated as standard deviation divided by the average) for hydrogen production rate and yield was less than about 15%. As summarized in Table 1, the hydrogen production rate averaged 1.75 L/h. The glucose conversion in the system was almost 100%. The hydrogen content in the biogas was around 60% with the balance $CO_2$.

TABLE 1

Summary of steady state data during dark fermentation mode (values are an average with ± standard deviation indicated).

| | Dark Fermentation Mode |
|---|---|
| Total Gas (L/h) | 2.9 ± 0.4 |
| Hydrogen Gas (%) | 60 ± 5 |
| Hydrogen Gas (L/h) | 1.75 ± 0.25 |
| Hydrogen Gas (L/L/h) | 0.35 ± 0.05 |
| Yield (mol $H_2$/mol glucose) | 2.8 ± 0.2 |
| Glucose Conversion (%) | 99.9 ± 1.5 |
| % COD removed | 40 ± 10 |

The biomass concentration in the reactor is an important operational parameter that affects both system stability and hydrogen yield. The average concentration of VSS in the biohydrogen reactor was 3900 mg/L. The COD mass balance, computed considering the measured influent and effluent CODs, and the equivalent CODs for both gas and biomass, are shown in Table 2. The closure of COD balance at 94% validates the reliability of the data. During the overall operational period the main liquid by-products were acetate, butyrate, and propionate at average concentrations of 2050 mg/L, 1150 mg/L, and 380 mg/L, respectively.

TABLE 2

Summary of products and COD mass balance

| Measured parameters | Dark Fermentation Mode |
|---|---|
| VSS reactor (mg/L) | 3900 ± 410 |
| VSS out (mg/L) | 680 ± 50 |
| VSS out (mg COD/L) [a] | 965 ± 100 |
| SCOD out (mg/L) | 5100 ± 750 |
| Acetate (mg/L) | 2050 ± 250 |
| Propionate (mg/L) | 380 ± 90 |
| Isobutyrate (mg/L) | 0 |
| Butyrate (mg/L) | 1150 ± 210 |
| Isovalerate (mg/L) | 0 |
| Valerate (mg/L) | 0 |
| Ethanol (mg/L) | 0 |
| Lactate (mg/L) | 0 |
| VFA (mg COD/L) | 4860 |
| Glucose Out (mg/L) | 0 |
| Hydrogen Gas (L/h) | 1.75 ± 0.25 |
| Hydrogen Gas (g COD/h) [b] | 1.1 |
| COD balance (%) [c] | 94 ± 8 |

[a] Based on 1.42 g COD/g VSS
[b] Based on 8 g COD/g H2
[c] COD balance (%) = ((VSSout (g COD/d) + H2 (g COD/d) + SCODout (g COD/d))/(TCODin (g COD/d))

System Performance During Power Application Mode

After 3 days of start-up of dark fermentation mode, and when hydrogen production was steady at 1.75 L/h, an external voltage of 1.0 V was applied to the four electrodes using four separate power supplies. The voltage was applied in cyclic mode for 4 hours per day. A total of 12 cycles of voltage application were applied over a period of 12 days. During power application cycles, acetate consumption and hydrogen content and volume were monitored.

Figure 5:
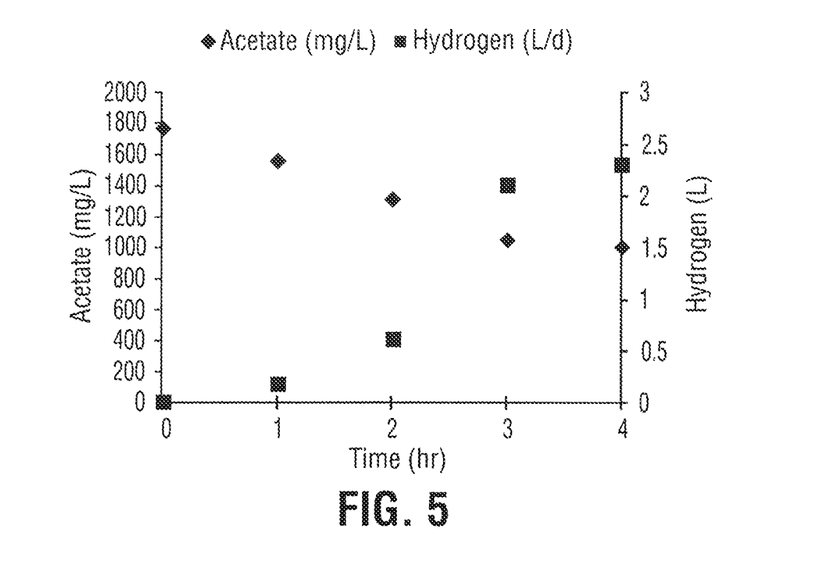
FIG. 5 is a plot of acetate consumption and hydrogen production during a tenth cycle of voltage being applied to an electrobiohydrogenator reactor.
Figure 6:
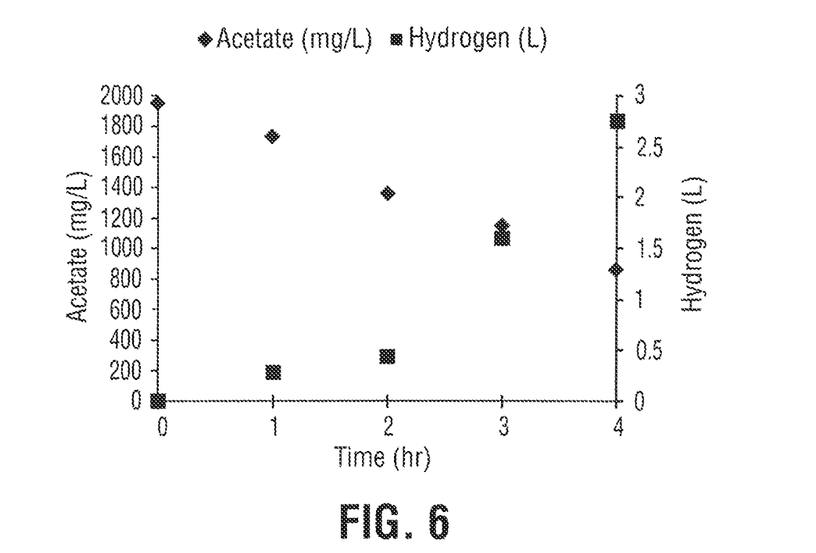
FIG. 6 is a plot of acetate consumption and hydrogen production during an eleventh cycle of voltage being applied to the electrobiohydrogenator reactor of FIG. 5.
Figure 7:
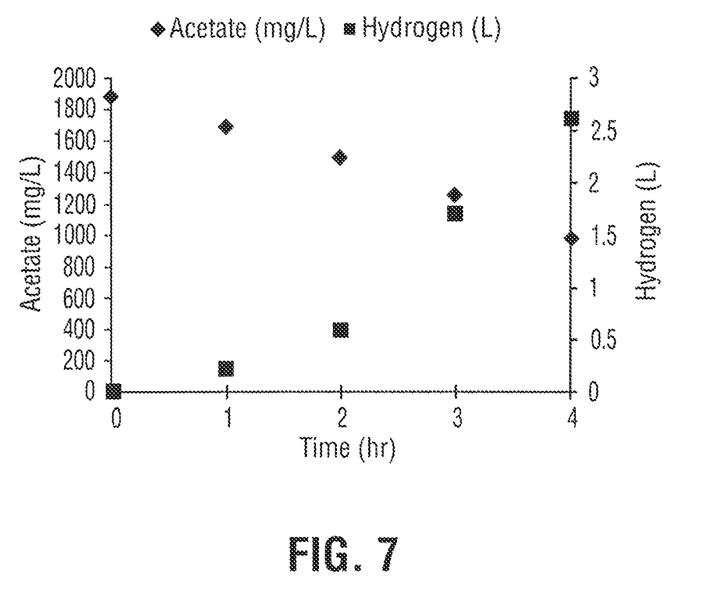
FIG. 7 is a plot of acetate consumption and hydrogen production during a twelfth cycle of voltage being applied to the electrobiohydrogenator reactor of FIG. 5.

FIGS. 5 to 7 show the acetate consumption and volumetric hydrogen production for cycles 10, 11, and 12 of power application, respectively. The acetate concentrations showed a declining trend from about 2000 mg/L to 1000 mg/L (50% reduction) over a period of 4 hr. In each of the last 3 cycles, the acetate consumption was around 10%, 20%, 35%, and 50% at 1 hr, 2 hr, 3 hr, and 4 hr, respectively. Volumetric hydrogen production an increasing trend and reached a maximum of 2.9 L.

As shown in Table 3, the average hydrogen content in the headspace was 65%. The maximum volumetric hydrogen production rate was 0.8 L/h. Acetate conversion averaged 57.6%. Based on the amount of hydrogen gas produced and acetate consumed an average hydrogen yield of 1.53 mole $H_2$/mol acetate was achieved (38% of theoretical). The COD removal efficiency was close to 45%.

TABLE 3

System performance during power application mode (values are an average with ± standard deviation for the last 3 cycles of power application indicated).

|  | Power application Mode |
| --- | --- |
| Total Hydrogen Gas (L) | 2.6 ± .3 |
| Hydrogen Gas (%) | 65 ± 8 |
| Hydrogen Gas (L/h) | 0.65 ± .15 |
| Hydrogen Gas (L/L/h) | 0.132 ± .038 |
| Yield (mol $H_2$/mol Acetate) | 1.53 ± 0.3 |
| Acetate Conversion (%) | 57.6 ± 6 |
| % COD removed | 43 |

CONCLUSIONS

The following conclusions can be drawn from the experiment with application of both dark fermentation and power application:
the overall maximum hydrogen yield that was achieved in process was 6.66 mol $H_2$/mol glucose;
the overall COD removal efficiency was around 77%; and
$H_2$ content of biogas ranged from 60% to 65% and hydrogen production rate from 0.132 L/L/h to 0.35 L/L/h.

Examples Only

For purposes of illustration and not limitation, an integrated method and system for hydrogen and methane production from industrial organic waste and biomass is disclosed herein. As required, embodiments of the method and system are disclosed herein. However, the disclosed embodiments are merely exemplary, and it should be understood that the method and system may be embodied in many various and alternative forms.

The figures are not to scale and some features may be exaggerated or minimized to show details of particular features while other features may have been eliminated to prevent obscuring aspects. Therefore, specific structural and functional details disclosed in the figures are not to be interpreted as limiting but merely as a basis for the claims and as a representative basis for teaching one skilled in the art to variously employ the present method and system.

The scope of the claims should not be limited by particular embodiments set forth herein, but should be construed in a manner consistent with the specification as a whole.

What is claimed is:

1. A method for producing hydrogen from bio-organic material by microbial electrolysis, comprising:
generating a dark fermentation broth by providing bio-organic material and anaerobic, hydrogen-producing microorganisms into a completely mixed bioreactor for breaking down the bio-organic material by dark fermentation into products including $H_2$, $CO_2$, fatty acids, and alcohols;
recovering at least a portion of the $H_2$ and of the $CO_2$ from the completely mixed bioreactor;
recovering a first liquid effluent from the completely mixed bioreactor, the first liquid effluent including at least a portion of the hydrogen-producing microorganisms, the fatty acids, and of the alcohols;
providing at least a portion of the first liquid effluent into a separator for separating into a concentrated biomass including at least a portion of the hydrogen-producing microorganisms and a second liquid effluent including at least a portion of the fatty acids and the alcohols;
recycling at least a portion of the concentrated biomass from the separator back into the completely mixed bioreactor; and
applying an input voltage to at least one of the completely mixed bioreactor and the separator for facilitating an electrobiohydrogenesis process in the at least one of the completely mixed bioreactor and the separator.

2. The method of claim 1, wherein the separator is a gravity settler.

3. The method of claim 2, wherein applying the input voltage comprises applying the input voltage to the completely mixed bioreactor.

4. The method of claim 2, further comprising recovering at least a portion of the $H_2$ and of the $CO_2$ from the gravity settler.

5. The method of claim 4, wherein applying the input voltage comprises applying the input voltage to the gravity settler, and the method further comprises recovering at least a portion of $H_2$ and $CO_2$ produced by electrobiohydrogenesis in the gravity settler.

6. The method of claim 5, wherein the temperature in the gravity settler is maintained at between about 20° C. and about 70° C.

7. The method of claim 1, wherein the temperature in the completely mixed bioreactor is maintained at between about 20° C. and about 70° C.

8. The method of claim 1, wherein the input voltage is between about 0.5 V and about 1.8 V.

9. The method of claim 8, wherein the input voltage is about 1.0 V.

10. The method of claim 1, wherein the input voltage is a continuous voltage.

11. The method of claim 1, wherein the input voltage is an intermittent voltage.

12. The method of claim 1, further comprising providing the second liquid effluent into a biomethanator for production of methane from the second liquid effluent.

13. The method of claim 12, further comprising providing the second liquid effluent into a storage tank prior to providing the second liquid effluent into the biomethanator.

14. The method of claim 12, wherein the temperature in the biomethanator is maintained at between about 20° C. and about 70° C.

15. The method of claim 1, wherein the anaerobic, hydrogen producing microorganisms comprise one or more of the species selected from the group consisting of *C. acetobutyricum, B. thuringiensis*, and *C. butyricum*.

\* \* \* \* \*